United States Patent [19]

Mohr et al.

[11] Patent Number: 5,515,294
[45] Date of Patent: May 7, 1996

[54] METHOD AND APPARATUS FOR TESTING COILED MATERIALS

[75] Inventors: Henry G. Mohr; Daniel W. Martin; Steven M. Montague; Henry Zapletal, all of Carthage, Mo.

[73] Assignee: L & P Property Management Company, Chicago, Ill.

[21] Appl. No.: 257,925

[22] Filed: Jun. 10, 1994

[51] Int. Cl.⁶ ........................................... G01B 5/30
[52] U.S. Cl. .................................... 364/508; 73/826
[58] Field of Search ................................ 364/508, 506, 364/507, 558; 73/788–860

[56] References Cited

U.S. PATENT DOCUMENTS

| | | | |
|---|---|---|---|
| 3,948,091 | 4/1976 | Voll | 73/806 |
| 4,031,746 | 6/1977 | Furuta et al. | 73/800 |
| 4,081,994 | 4/1978 | Yamawaki et al. | 73/806 |
| 4,480,482 | 11/1984 | Henry et al. | 73/805 |
| 4,841,779 | 6/1989 | Mitsuhashi et al. | 73/826 |
| 5,154,085 | 10/1992 | Takeda | 73/811 |
| 5,203,206 | 4/1993 | Shofner et al. | 73/828 |

FOREIGN PATENT DOCUMENTS

| | | |
|---|---|---|
| 0412348 | 2/1991 | European Pat. Off. . |
| 161636 | 10/1982 | Japan . |
| 169739 | 7/1986 | Japan . |
| 1325319 | 7/1987 | U.S.S.R. . |

OTHER PUBLICATIONS

Proceedings Of The Annual Conference Of The Engineering In Medicine And Biology Society, Philadelphia, Nov. 1–4, 1990, vol. 12; 1990, 1 Nov. 1990 Pedersen P. C.; Banu Onaral, pp. 2085–2086, XP 000238965, "Life Prediction Of Cardiac Leads Under Cyclic Loading", Charles Martin, et al.

Research Disclosure, No. 255, Jul. 1985 Havant GB, p. 379, Disclosure No. 25562, J. S. Peraro et al.

*Primary Examiner*—James P. Trammell
*Attorney, Agent, or Firm*—Wood, Herron & Evans

[57] ABSTRACT

A curved sample of material is tested for ultimate tensile stress and elongation without prestraightening or premarking of the length of the sample. The sample is gripped at its ends and positioned to extend over convex surfaces mounted adjacent to the grippers on a pair of longitudinally moveable members. The members are moved apart and incremental data of the relative distances between the convex surfaces, representing the length of the sample, are stored. With each of the distance measurements, tensile stress measurements in the wire are made and stored. After the wire breaks, the data is analyzed. The stress versus distance ratios and rates of changes are analyzed to determine the end points of the stress versus length curve for the elastic deformation region, which is taken to begin when the wire has been pulled straight as is detected by a sudden increase in ratio of the tensile force versus sample length, and to end by a decrease the ratio, at the yield point where plastic deformation or permanent elongation of the sample begins. The permanent elongation of the sample ends at the break point of the sample, when it is at its total elongation.

18 Claims, 3 Drawing Sheets

METHOD AND APPARATUS FOR TESTING COILED MATERIALS

The present invention relates to the testing of coiled materials, and particularly to tensile strain or elongation testing of materials such as wire that are typically wound on a spool or in a coil.

BACKGROUND OF THE INVENTION

In product manufacture, determination and maintenance of the exact physical properties of the basic materials of which the product is made may be critical to the quality of the manufactured product. In the manufacture of coil springs, for example, the manner in which the material of which the springs are made deforms, both elastically and plastically, in response to loads applied in the manufacturing and in the use of the springs determines, in part, the useful life and performance of the spring and the ultimate product in which the spring becomes a part.

In the manufacture of such coil springs, which are typically made of metal wire, stress and strain properties of the basic wire material, when subjected to tensile forces must be known and maintained at certain design criteria. Such properties include the yield and tensile strengths of the wire, and the total and permanent tensile strains, or elongations under critical loads of the wire material of which the springs are made. Accordingly, regular periodic testing of the wire material during the product manufacturing process is essential to controlling quality in the product manufacturing operation.

Frequently, metal wire, metal sheet material and other types of such materials are supplied in coils. As a result, material removed from the coils often possesses a permanent or preset bend or curvature that reflects the permanent or plastic deformation that was imparted to the material when it is wound into a coil. This curvature has been an impediment to the accurate testing of such materials.

In the testing of coiled materials, for example in the elongation testing of high carbon steel wire used in the formation of certain types of springs such as often used for the springs for mattresses and box spring units, a sample of wire to be tested is removed from the coil and, before testing is carried out, is straightened. Then the straightened sample of wire is measured and some standard length is marked on the sample. Typically, the straightening and marking is carried out manually. The marked straightened length of wire is then placed in a tensile testing device and the sample is pulled to the breaking point. The distance between the two marks immediately prior to the breaking of the sample is taken as the total elongated length of the wire, and is due to both elastic and plastic deformation prior to breaking. This length, divided by the initial length, is the total elongation of the material. Then the two parts of the broken wire are placed into contact with each other at the failure point and the length between the two marks is measured. This length is the permanent or plastic deformation component of the total deformation. It is a number representing the fractional change in original length as calculated in accordance with ASTM standard A 370.

Several steps in the conventional elongation measurement process contribute to error in the measurement of elongation. The straightening of the wire, which is difficult to perfectly achieve, results in an error in the measurement of initial length. Imprecise straightening may result in some slack in the sample that adds to the initial length. Similarly, the marking procedure contributes to such error in establishing the initial length that is measured. The procedure of abutting the severed ends of the sample, following the test, to reconstruct the total deformed length prior to failure introduces error in the deformed length measurement. Overall, the measurement process is time consuming.

Various other methods have been devised to facilitate the testing of yield and tensile strengths and total and permanent elongation of various forms of materials. However, an easy to perform, quick and reliable method of performing periodic testing of coiled materials that have developed a permanent deformation or curvature when coiled remains a problem in manufacturing processes where the properties of such materials must be routinely monitored.

Accordingly, there remains a need for better, more accurate and more reliable methods for testing the material properties of coiled and other materials that develop a curvature for storage or transportation purposes.

SUMMARY OF THE INVENTION

A primary objective of the present invention is to provide a method and apparatus by which the physical properties of an elongated material, the length of which has a permanent curvature when in an unstressed state, can be tested without prestraightening a sample of the material along the length being tested. It is a particular objective of the present invention to provide an accurate method of testing elongation, particularly the total and permanent elongations, of a sample of curved material, such as a wire material that has been wound in a coil, where the length of the sample has a permanent curvature when the test is begun.

In accordance with the principles of the present invention, a preferred embodiment of testing apparatus is provided with grippers to engage the opposite ends of a sample of a length of the wire or other material to be tested. The grippers are inclined to receive the curved sample in an unstressed curved condition and to lock the ends in place. The grippers are mounted on members that move longitudinally relative to each other, driven by a ball screw mechanism, so the members can be driven apart at a controlled rate to subject the sample to tension and stretch it until it breaks.

Further in accordance with the preferred embodiment of the apparatus, the grippers are each provided with a solid curved surface, such as a cylindrical capstan or curved anvil, immediately adjacent thereto, that lies under the arched curvature of a sample held in the grippers and in a line parallel to the longitudinal axis of the apparatus and direction of motion of the members relative to each other.

In accordance with the preferred method of the present invention, after the sample is mounted in the grippers, the members move apart. As the members move, the gripped sample is pulled over the curved surfaces and into a straight line that is tangent to the curved surfaces and parallel to the direction of relative motion of the members. Then the sample is pulled further to stretch elastically to its yield point and then plastically until the material ultimately fails and the sample breaks in two parts. The members are driven apart at a first and faster speed until the sample has straightened, and then at a second and slower speed until the sample breaks, at which point the drive stops, In the preferred method and apparatus of the invention, as the members holding the ends of the sample move apart from where the sample is held in an unstressed condition, a digital encoder on a drive member shaft produces a series of readings that are stored in a digital memory, each reading representing a precise distance between the tangent points of the sample with the curved surfaces. Simultaneous with each measurement of distance, a load cell connected in series with the sample measures the total tension or tensile load on the sample and a digital representation of the measurement is stored in the digital memory in direct correlation with the stored distance value.

Further, as the values of load and distance are stored, a load versus length function is digitally represented in which the load values increase slowly, with each increase in sample length, at first until the sample has straightened, whereupon the load values rise sharply as the straightened wire is deformed elastically by the tension on the sample. This increasing force is usually an approximately linear function of elongation, with the slope being a constant that is directly related to the modulus of elasticity of the material. As the material of the sample reaches its elastic limit, generally defined as the yield point of the material, and begins to deform plastically, the rate of change of force to elongated distance declines. For some materials, the force itself might even decline as the material cross-section is reduced in the course of the elongation of the material. Ultimately the material breaks.

Further in accordance with the preferred embodiment of the method of the invention, the load values are sensed and, when they suddenly drop to zero, the movement of the members in the apparatus is automatically stopped. Thereupon, after the test is completed and all the data has been taken and stored, with the aid of a programmed digital computer, the load values and distance values from the digital memory are analyzed.

The data analysis includes the step of detecting the point at which the sample is straightened and begins to stretch elastically. This detection is made by recognizing a substantial increase in the rate of change of force in the sample per incremental change in sample length. The length of the sample at this point is taken as the straightened length of the sample. This may be achieved by a threshold test of the force, for example, by detecting when the load measurement value first exceeds a value of a preset and stored threshold value. For stiff spring wire of the type used in mattresses, for example, such a threshold value may be, for example, thirty or thirty-five pounds.

Then, the yield point of the sample is detected as the point at which the rate of change of the tensile force in the sample per incremental change in sample length begins to decrease. Once these two points are detected, the precise slope of the load versus length curve is calculated at a length approximately midway between the two points, and the endpoints of the elastic deformation are recalculated based on the calculated slope. The length difference in distance between the two points divided by the straightened length of the sample produces a value for the elastic elongation of the material. The difference between the length of the sample immediately before the break point and the length of the sample at the yield point, divided by the initial straightened length, produces a value for the permanent or plastic elongation of the material. The sum of the permanent and elastic elongations of the material equal the total elongation of the material. These elongation values are stored in the computer memory, displayed to the operator and may be printed out as a record of the test.

In addition, stress values of the material may be similarly output based on information generated in the testing method of the invention. The yield stress may be calculated by dividing the tensile force at the yield point by the initial cross sectional area of the sample, and the ultimate tensile stress may be calculated by dividing the maximum tensile force read before the breaking of the material by the initial cross sectional area of the sample.

The method and apparatus of the invention provides an accurate method that can be efficiently performed on curved samples of material such as spring wire removed from a coil, without first straightening the sample or premarking a running length of the sample for testing. The equivalent straightened length of the sample is effectively and accurately determined automatically from an unstressed curved sample for use in the performance of a stress test on the sample to determine elongation and stress parameters.

These and other objectives and advantages of the present invention will be more readily apparent from the following detailed description of the drawings and preferred embodiments, in which:

BRIEF DESCRIPTION OF THE DRAWINGS

FIG. 1A is a fragmentary view of a portion of the apparatus of FIG. 1 illustrating the members holding the ends of the sample are moved apart to where the sample is in a straightened condition.

FIG. 1B is a fragmentary view of a portion of the apparatus of FIG. 1 illustrating the members moved further apart to where the sample is broken.

DETAILED DESCRIPTION OF THE PREFERRED EMBODIMENTS

Figure 1:
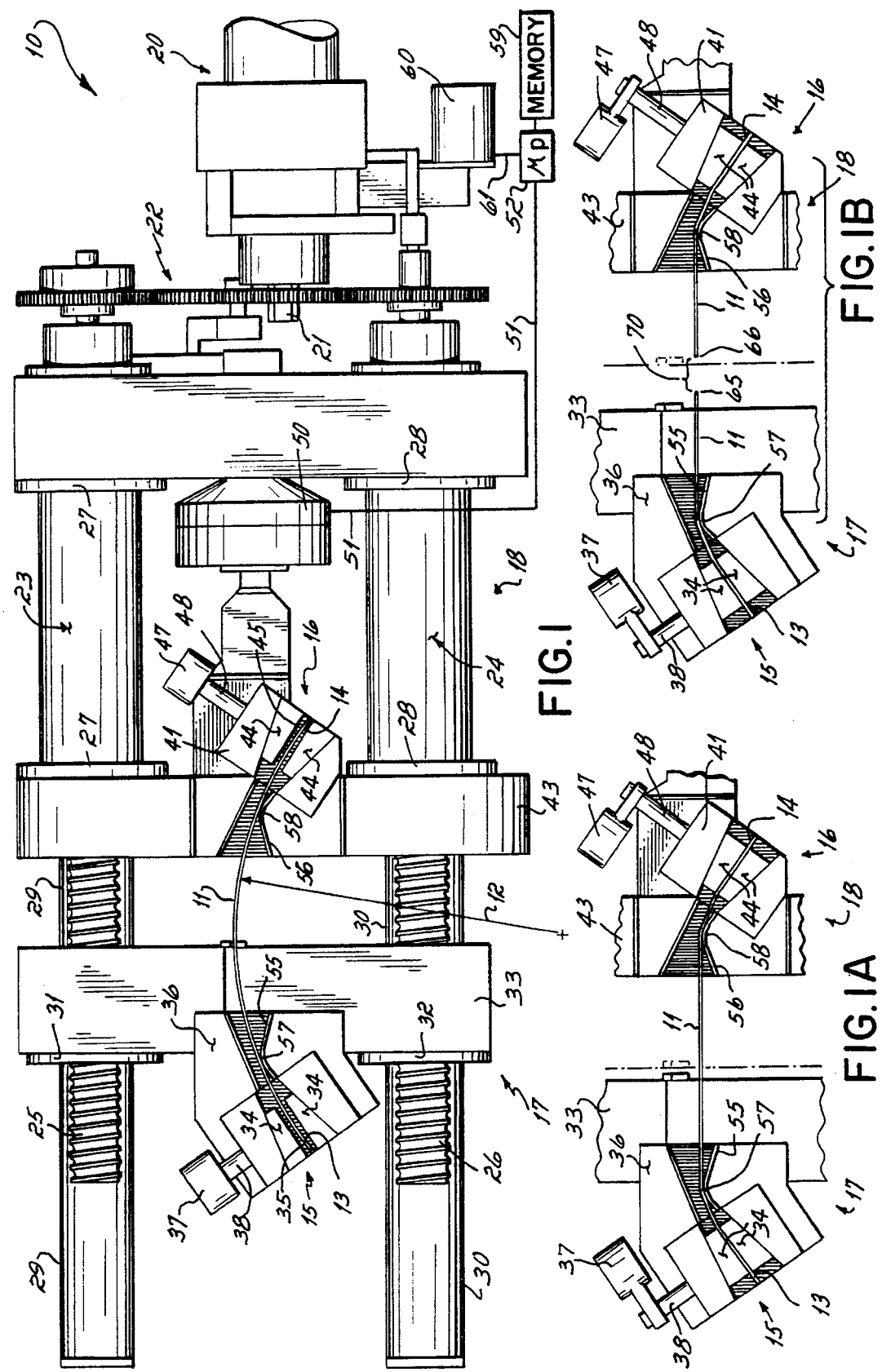
FIG. 1 is an elevational view of one preferred embodiment of an elongation testing apparatus according to principles of the present invention, illustrating components of the apparatus in initial positions in which an unstressed arcuate sample of a coiled wire has been placed for subsequent gripping and testing.

Referring to FIG. 1, an apparatus 10 according to one embodiment of the present invention is illustrated. The apparatus 10 of the illustrated embodiment is useful for testing the properties of coiled or otherwise curved linear material. In the context of this specification, the material referred to is that of a type furnished in running lengths such as wire, sheet metal or other similarly linear or elongated substance used in manufacturing. Such materials are provided in generally long but thin lengths, and will therefor bend much more easily when subjected to a transverse force than they will stretch longitudinally when subjected to a tensile force of the same order of magnitude. Such materials, particularly wire materials from which steel springs are made, are frequently furnished to manufacturers in long lengths rolled in coils, frequently wrapped around a spool or roll. The wire in these coils, though relatively elastic, is often imparted, either unavoidably or intentionally, with a permanent bend throughout its length as it is wound into the coil, thereby causing the wire to spring to an arcuate curved shape when it is uncoiled and returned to an unstressed condition.

In FIG. 1, a sample of such a material, depicted as a length of hard steel spring wire 11, is illustrated as approximately fifteen inches long and having an arcuate shape, in its unstressed state, of a radius of curvature 12 of, for example, roughly twenty inches. The sample or wire 11 is illustrated as supported in the apparatus 10 with opposite ends 13 and 14 of the wire 11 respectively held in a pair of gripper assemblies 15 and 16. The gripper assemblies 15 and 16 are respectively mounted on a pair of members, including a carrier member 17 and base support member 18, which are longitudinally spaced from each other and longitudinally moveable with respect to each other.

Preferably the support member 18 is a stationary member on which is rigidly supported a DC variable speed motor 20. The motor 20 has an output shaft 21 linked through a gear drive 22 to a plurality of ball screw assemblies, shown in FIG. 1 as two in number, 23 and 24, carried by the support member 18. Each of the ball screw assemblies 23 and 24 has a respective rotary ball screw shaft 25 and 26, extending longitudinally from the support member 18 and supported therein on respective sets of roller bearings 27 and 28.

The carrier member 17 is journaled to the ball screw shafts 25 and 26 by a pair of ball nuts 31 and 32, so that, as the ball screw shafts turn, in motion synchronized by the gear drive 22, the carrier member 17 moves longitudinally relative to the support member 18, moving the gripper assemblies 15 and 16 either together or apart on ways 29 and 30. The support member 17 is mounted to slide relative to the support member 18, preferably on bearings, (not shown) on the ways 29 and 30 that are fixed relative to the support member 18.

One of the gripper assemblies 15 is rigidly supported on a carrier block 33 which houses the ball nuts 31 and 32. The gripper assembly 15 has a set of jaws 34 that define a material receiving orifice or gap 35 that is configured to receive the end 13 of the wire sample 11. The jaws 34 are mounted on the carrier block 33 by a bracket 36 configured such that the orifice 35 is generally inclined at an angle relative to the longitudinal axis of the apparatus 10 that is generally tangent to the end 13 of the wire 11 when the wire 11 is mounted in the grippers 15 and 16. The longitudinal axis of the apparatus 10 is generally defined as a line parallel to the axes of the ball screw shafts 25 and 26, which is the direction of movement of the carrier member 17 relative to the support member 18. The jaws 34 of the gripper assemblies 15 are actuated to grip the end 13 of the wire 11 by the manual rotation of an actuator knob 37 linked to the jaws 34 through a pinion assembly 38.

The other one of the gripper assemblies 16 is supported on a floating block 41 mounted to slide on a support block 43 in bearings or other low friction elements (not shown) while transmitting substantially no longitudinal force between the floating block 41 and the support block 43. The support block 43 is preferably stationary and carries the forward sets of the roller bearings 27 and 28 which support the ball screw shafts 25 and 26. The gripper assembly 16 is substantially a mirror image of the gripper assembly 15, and also has a set of jaws 44 that define a material receiving orifice or gap 45 configured to receive the opposite end 14 of the wire 11. The jaws 44 are mounted on the floating block 41 such that the orifice 45 is generally inclined at an angle that is equal to and opposite the angle of inclination of the orifice 35 relative to the longitudinal axis of the apparatus 10. The jaws 44 are actuated to grip the end 14 of the wire 11 by the manual rotation of an actuator knob 47 linked to the jaws 44 through pinion assembly 48.

The floating block 41 is longitudinally supported through a load cell 50 on the support member 18 so that, when the members 17 and 18 are moved apart, substantially all of the longitudinal force exerted between the floating block 41 and support block 43 will equal the tension on the wire 11. This tension is thus measured by the load cell 50, which produces a load signal in analog electrical form that has a value directly related to the total tensile force in the wire. The load cell 50 is provided with an output 51 that connects through an appropriate interface circuit (not shown) that includes an analog to digital converter to an input of a computer based programmed microprocessor 52. The microprocessor 52 receives the load signal and stores digital values of tensile force measurements from the load cell 50. Each of these force values is correlated with a digital value associated with the length or elongation of the wire 11, which is also digitally stored, that is produced in a manner described below.

Each of the gripper assemblies 15 and 16 is provided with a rotary capstan or, as shown, a fixed anvil 55 and 56, respectively, each having a convex outer surface that is curved to a radius relatively large in relation to the thickness of the material, or diameter of the wire 11, and preferably to a radius that is less than the radius 12 of the wire curvature. The anvils 55 and 56 are rigidly mounted to the respective carrier and floating blocks 33 and 41, close to the gripper jaws 34 and 44, respectively, so as to lie in close proximity to the wire 11, when the wire 11 is inserted in its unstressed curved condition into the jaws 34 and 44. The anvils 55 and 56 are located within arc formed by the curvature of the wire 11, that is, on the concave side thereof of the unstressed wire 11. Each anvil 55 and 56 has a respective tangent point 57 and 58 on the surface thereof to which a common longitudinally extending line or plane, parallel to the ball screw shafts 25 and 26, is tangent. Preferably, the anvils 55 and 56 provide enough frictional engagement with the wire 11 so that, as the anvils are moved apart, the tension that develops in the wire 11 is significantly greater between the two points 57 and 58 than between the respective points 57 and 58 and the gripper jaws 34 and 44, so that no significant elongation, or at least no permanent elongation or breaking of the wire, occurs between the gripper jaws 34 and 44 and the respective points 57 and 58.

The apparatus 10 is provided with an encoder 60, preferably in the form of a resolver of the rotary optical type. The encoder 60 precisely measures the angular position of a shaft of the gear drive 22 or of the ball screw assemblies 23 and 24 to produce a displacement signal that is directly and linearly proportional to the distance between the tangent points 57 and 58 on the anvils 55 and 56. The encoder 60 generates a displacement signal in the form of a series of digital pulses, each representative of a fixed incremental change in the distance between the points 57 and 58 as the members 17 and 18 are moved relative to each other. This deformation signal is communicated on an output line 61 to an input of the microprocessor 52, which stores a series of position values, one associated with each position at which the tensile force values are measured and stored. Preferably, as the members 17 and 18 are moved apart during a test of a wire sample 11, incremental values of the displacement signal are read and stored, and with each such displacement signal value that is read, the load signal is simultaneously read and a corresponding tensile force value is stored. In the initial positions of FIG. 1, the displacement signal value is a reading of the distance between the points 57 and 58 when the wire 11 is in its unstressed condition, and thus the load signal value is approximately zero.

FIG. 1A illustrates the positions of the members 17 and 18, grippers 15 and 16, points 57 and 58 and the wire 11 when the carrier member 17 has been moved away from the support member 18 after the wire has been locked in the jaws 34 and 44 at an initial position of the carrier member 17 as illustrated in the phantom line in FIG. 1A. In the position illustrated in this figure, the wire 11 has been pulled to the point that it is generally straight, lying in a line that is tangent to the anvils 55 and 56 at the respective points 57 and 58 on the surfaces thereof. At this position, the displacement signal value represents the running length of the wire sample 11, or the length of the straightened wire. The load signal value at this position will represent the relatively small tensile force on the wire that is sufficient to cause the wire to straighten against the internal elastic forces needed to overcome the imparted initial curvature of the wire 11.

FIG. 1B further illustrates the positions of the same elements after the carrier member 17 has been moved further relative to its initial position (shown in phantom) and the wire 11 has broken. As shown in FIG. 1B, after the wire 11 has broken, severed ends 65 and 66 thereof have separated to form a gap 70 having a dimension equal at least to the material relaxation from the elastic deformation of the wire 11. At the instant of breaking of the wire, the deformation signal value will be equal to a number representing the total elongated length of the wire 11. The maximum load signal value recorded before the breaking of the wire will represent the ultimate tensile force of the wire which, if divided by the initial cross sectional area of the wire, will produce a number representing the ultimate tensile strength of the wire 11. Immediately after the breakage of the wire, the load signal value will be zero.

Figure 2:
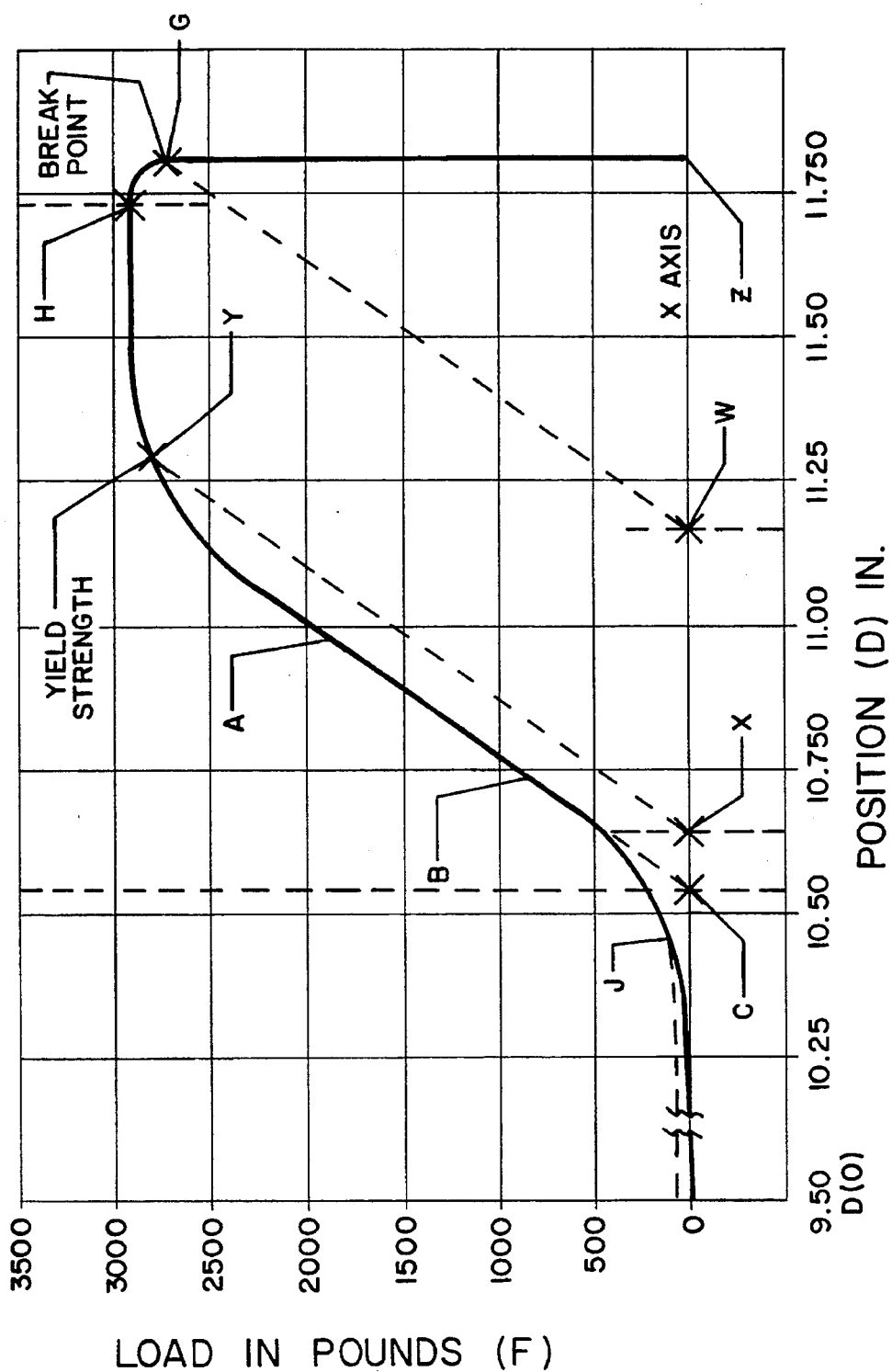
FIG. 2 is a chart illustrating tensile force versus elongated length of the sample in the operation of the apparatus of FIGS. 1–1B according to a preferred method of the invention.
Figure 3:
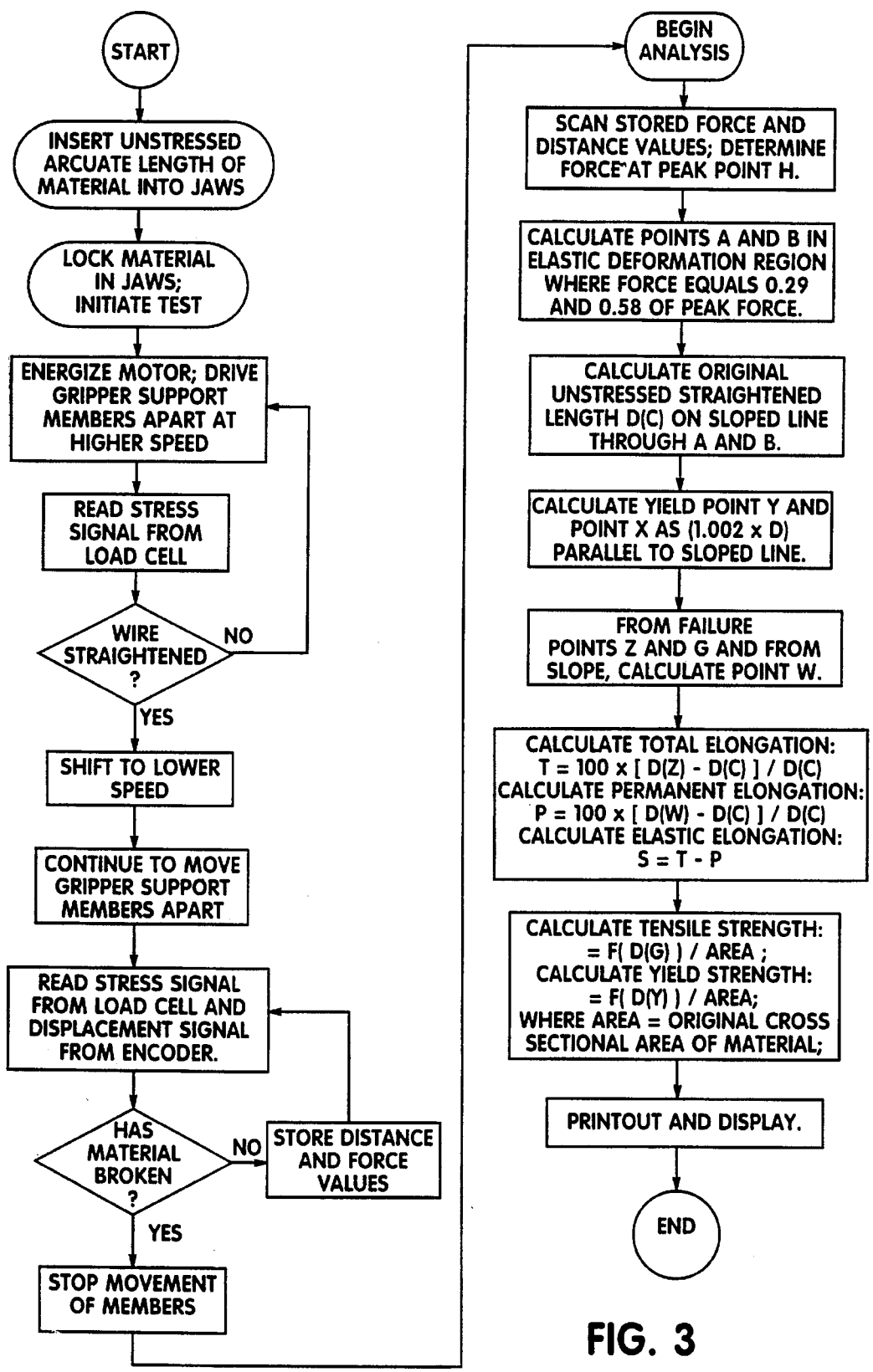
FIG. 3 is a flow chart of the preferred embodiment of the method of the present invention, including the steps performed under the control of the program of the processor portion of the apparatus.

The operation of the apparatus 10 will be understood with reference to the graph of FIG. 2 and the flow chart of FIG. 3. In the flowchart of FIG. 3, the operations preferably performed manually by an operator are illustrated in oval boxes while those preferably performed automatically under the control of the programmed microprocessor 52 are illustrated in parallelogram shaped boxes of various forms.

In the performance of the method of the preferred embodiment of the invention, an operator takes a sample of the material from a spool or coil and cuts it to a length suitable for testing, thereby forming, for example, the wire sample 11 of FIGS. 1–1B. This sample will have a preset curve, when in unstressed condition, due to plastic deformation that occurs when the material was coiled or spooled. The operator inserts the opposite ends 13 and 14 of this sample 11 in the respective jaws 34 and 44 of the gripper assemblies 15 and 16, and then locks the jaws 34 and 44 by turning the knobs 37 and 47. The sample 11 will assume the position and unstressed shape illustrated in FIG. 1. In this position and shape, the sample 11 extends between the gripper assemblies 15 and 16 and passes in close proximity to the anvils 55 and 56. The total running length of the material will, in this curved condition, be greater than the actual initial distance D(O) between the points 57 and 58. The distance D(O) may have a value of, for example, 9.500 inches, which is the distance to which the points 57 and 58 return at the end of each test, or when the operator otherwise presses a RETURN button on a console (not shown). The value of the distance D(O) is a predetermined constant stored in a computer memory 59 associated with the computer based microprocessor 52. The distance D is represented as the horizontal axis on the graph of FIG. 2. At the displacement or distance D(O), no tensile stress is present in the sample 11, and thus no force is detected by the load cell 50. Thus, at $D=D(O)$, the force F, which is represented in the graph of FIG. 2 as a function of the displacement D, is equal to zero: $F(D(O))=O$.

The operator then initiates the test by depressing a START button on the machine control console (not shown). When the test is initiated, a wire sample ID number and the a value of the wire diameter are either centered manually or, preferably, down-loaded through a serial port from a remote computer. Initiation of the test causes the DC motor 20 to be energized at a transport speed, which is the higher of two speeds, of, for example, two inches per minute. This causes the motor output shaft 21 to turn to drive the gear train 22 and rotate, in synchronism, the shafts 25 and 26 of the ball screw assemblies 23 and 24, respectively. As the shafts 25 and 26 turn, the carrier member 17 moves away from the support member 18. This movement causes pulses to be generated by the resolver or encoder 60, each pulse representing a fixed incremental unit of distance moved by the carrier member 17, which, when added to the initial distance D(O), equals the distance between the points 57 and 58. The pulses are generated at a rate of approximately 100 per second. Thus, these pulses are counted by the processor 52, adding the incremental units of length to the stored value for the initial distance D(O) between the points 57 and 58. Either the count, a number corresponding to the incremental distance represented by the count or the actual computed distance between the points 57 and 58 is stored in the memory 59 as a value of a displacement signal, represented by the horizontal axis in the graph of FIG. 2. At the higher speed, each increment of distance measurement is approximately 1/3000 inch.

As the points 57 and 58 move apart, the sample 11 extending between the grippers 15 and 16 begins to straighten. The resistance of the sample 11 to the straightening causes a small force to be detected by the load cell 50 as the tension in the sample 11 pulls the floating block 41 toward the carrier member 17 in the direction of its motion. This small force is represented by a value of force F in the graph of FIG. 2 that is slightly greater than zero. As the points 57 and 58 continue to move apart, the wire eventually assumes a straightened shape as illustrated in FIG. 1A. When this occurs, the tensile stiffness of the sample, which for an elongated or linear material as defined above is much greater than the bending stiffness of the material that was overcome during the straightening of the sample 11, has a longitudinal component that causes the force exerted on the load cell 50 to rise sharply. This occurrence is detected by analysis of the changing values of force F with the processor 52, either by identifying that the change of slope of the F(D) curve of FIG. 2 has abruptly increased, or by detecting that a threshold force, of for example 30 or 60 pounds, has been exceeded at the load cell 50. When the straightening of the wire sample 11 is so detected, an initial determination is made that elastic longitudinal deformation of the sample has begun. The point on the F(D) curve at which this occurs is represented by point J on the graph of FIG. 2. Thereupon it is concluded that the wire has straightened and is beginning to stretch longitudinally, and so the motor 20 is shifted to drive the member 17 relative to the member 18 at a lower speed of, for example, 0.5 inches per minute. At this lower speed, the pulses from the encoder 60 signal incremental distance changes of approximately 1/12,000 inch.

At the lower speed, the points 57 and 58 continue to move apart, stretching the sample 11 longitudinally. The total stretched length of the sample 11 is represented by the displacement signal values D in FIG. 2. The tensile force in the wire, during the elastic deformation, is sensed by load cell 50 and plotted and the function it(D) to the right of the point/I in FIG. 2, which is the steepest portion of the curve. As the points 57 and 58 move apart further, each incremental distance change is determined from the output of the encoder 60 and stored as a displacement signal value in the computer memory 61. For each recorded value of displacement, a corresponding force measurement signal value from the load cell 50 is recorded in also recorded in the memory 61.

The motion of the carrier member 17 away from the support member 18 continues until the material sample 11 breaks. The break will be detectable from the fact that the force measured by the load cell 50 drops suddenly to zero, indicated by point Z in the graph of FIG. 2. When this breaking has occurred, the signal to the motor 20 stops the motor 20 which terminates the movement of the carrier member 17 relative to the support member 18. The computer then proceeds to analyze the data stored from the corresponding measurements of distance and force.

Analysis of the stored values of D and F(D) is made by first determining more exactly the straightened unstressed length of the sample 11, which was previously only estimated as the distance to point J. This is accomplished by taking the highest value of the force reading, which occurs at a point indicated as point H on the graph of FIG. 2, and then finding two points/I and B on the curve of the function F where the force equals 0.29 and 0.58 of the peak force, respectively, or, where F(A)=0.29 F(H) and F(B)=0.58 F(H). The points A and B are marked in FIG. 2. These points are actually determined to be the first points at which the force values are recorded to equal or exceed the values of 0.29 and 0.58 of peak force respectively. Then, through the points A and B, the slope of a line is calculated, and the intersection of the calculated line with the F=0 line, or x-axis, is determined, as indicated by point C on the graph of FIG. 2. The distance D(C) represents the straightened unelongated length of the sample 11.

Next, a yield point Y is calculated. As a matter of definition, the yield point Y is established as the point where the length has departed from the line of constant slope, or linear elastic deformation, that extends through point C by 0.2% of the straightened unelongated length D(C) of the sample 11. This is determined by taking 1.002×D(C) on the F=0 line and defining point X such that D(X)=1.002 D(C). Then point Y is calculated as the intersection of a line through point X and parallel to the line through points A and B. This point Y is taken as the yield point of the material.

Then the values of the point at which the sample failed or broke are considered. The force measured immediately before the break of the material sample 11 is taken as the force measured four readings before a force value of zero was detected, which may be assumed, for example, as the dropping of the force reading to a value of less than some nominal value of, for example, 20 pounds. This count of four is selected to provide enough time for the zero reading to be detected following the breaking of the material. The point is indicated as point G in FIG. 2. Then, a point W is determined on the graph of FIG. 2 as the intersection with the F=0 line of a line through point W and parallel to the line through points A and B.

Then, elongations are calculated as follows: The total elongation, T is equal to the horizontal distance on the graph of FIG. 2 between, or the difference in the displacement values for, points C and Z, or, in terms of percentage of unstraightened undeformed length:

$$T=100\times[D(Z)-D(C)]/D(C).$$

The permanent or plastic portion of the elongation, P is the horizontal distance on the graph of FIG. 2 between points C and W, or:

$$P=100=[D(W)-D(C)]/D(C).$$

The elastic portion of the elongation, S, can also be calculated as the horizontal distance from points C and Y, which is equal to T−P.

Additionally, the yield strength is calculated as the force at point Y divided by the cross-sectional area of the sample 11, which can be calculated from the wire diameter value input into or stored in the computer memory 61

$$(area=F]=\Pi\times(diam/2)^2):yield\ strength=F(Y)/area.$$

Similarly, the ultimate tensile strength is calculated as the force at the peak point H divided by the cross-sectional area, or *tensile strength=F(H)/area*. The calculated values are stored, printed out and displayed to the operator. Preferably, all data from the test is transmitted through a serial port to the remote computer for storage, monitoring and analysis.

In the preferred embodiment, the graph illustrated in FIG. 2 is generated and displayed on a screen to the operator of the test as the data is available.

From the description above, those skilled in the art will appreciate that various additions and modifications can be made to the jig, and method to connect brackets to teeth with the jig, without departing from the principles of the present invention. Therefore, the following is claimed:

What is claimed is:

1. An apparatus for testing the properties of a curved linear material comprising:

a pair of members, including a support member and a carrier member, mounted for relative longitudinal movement toward and away from each other;

a motor supported on the support member having an output drive operatively linked between the support member and the carrier member so as to impart relative longitudinal movement between the carrier member and the support member;

a pair of grippers, each mounted on a respective one of the members and each inclined relative to the other to receive and tightly grip opposite ends of a length of a sample of material having an arcuate unstressed curvature, each of the grippers having mounted adjacent thereto on the respective member a convex surface positioned between the grippers and proximate the sample gripped therein, each convex surface having a point thereon tangent to a common longitudinal line inclined relative to the grippers, each of the points thereby being relatively longitudinally moveable in direct relation to relative movement between the members;

an encoder operatively linked to the members to generate a displacement signal having discrete values each directly related to a relative distance between the points;

a load sensor arranged to measure longitudinal tensile force in the sample and to generate a load signal having discrete values each directly related to a longitudinal force measurement;

a digital memory having inputs connected to the encoder and to the sensor to store data of a plurality of load signal values as a function of displacement signal values; and a program controlled processor having an input connected to the memory and responsive to characteristic changes in the force measurement data as a function of the relative distance.

2. The apparatus of claim 1 wherein:

the motor output drive includes at least two parallel synchronously geared ball screw drives linking the members.

3. The apparatus of claim 1 wherein:

each of the convex surfaces has a radius of curvature that is large with respect to the thickness of the material and is less than the radius of arcuate curvature of the material.

4. The apparatus of claim 1 wherein the program controlled processor includes programmed logic devices responsive to the stored displacement signal values and load signal values, as the members are moved apart, so as to:

determine, in response to a substantial decrease in the measured force, a displacement signal value and a force measurement value corresponding to the breaking of the material and associated respectively with the total elongation and tensile strength of the material;

determine, from a substantial increase in the rate of change of the measured force signal to rate of change of the displacement signal, a measured distance between the points on the convex surfaces that defines an initial length of the sample when the sample has straightened and begun to elastically elongate; and determine, from a significant decrease in the rate of change of the measured force signal to rate of change of the displacement signal, a displacement signal value corresponding to a measured distance between the points on the convex surfaces that corresponds to the beginning of plastic deformation of the sample and defines an elastic elongation of the material, and a force measurement value associated with the yield strength of the material.

5. An apparatus for testing the properties of a curved linear material comprising:

a pair of members, including a support member and a carrier member, mounted for relative longitudinal movement toward and away from each other;

a motor having an output drive operatively linked between the support member and the carrier member so as to impart relative longitudinal movement between the carrier member and the support member;

a pair of grippers, each mounted on a respective one of the members and each positioned and oriented to receive and tightly grip opposite ends of a length of a sample of material having an arcuate unstressed curvature, each of the grippers having mounted adjacent thereto on the respective member a surface positioned between the grippers and proximate the Sample gripped therein, each surface having a point thereon tangent to a common longitudinal line spaced transversely of the grippers, each of the points thereby being relatively longitudinally moveable in direct relation to relative movement between the members;

an encoder operatively linked to the members to generate a displacement signal having discrete values each directly related to a relative distance between the points.

6. The apparatus of claim 5 wherein the program controlled processor includes programmed logic devices responsive to the stored displacement signal values and load signal values, as the members are moved apart, so as to:

determine, in response to a substantial decrease in the measured force, a displacement signal value and a force measurement value corresponding to the breaking of the material and associated respectively with the total elongation and tensile strength of the material;

determine, from a substantial increase in the rate of change of the measured force signal to rate of change of the displacement signal, a measured distance between the points on the surfaces that defines an initial length of the sample when the sample has straightened and begun to elastically elongate; and determine, from a significant decrease in the rate of change of the measured force signal to rate of change of the displacement signal, a displacement signal value corresponding to a measured distance between the points on the convex surfaces that corresponds to the beginning of plastic deformation of the sample and defines an elastic elongation of the material, and a force measurement value associated with the yield strength of the material.

7. The apparatus of claim 6 wherein:

the processor is programmed to derive a constant corresponding to an elastic modulus for the sample from a derived linear relation of the tensile force of a values of longitudinal force and distance at a distance approximately midway between the initial length and the elastic elongation.

8. The apparatus of claim 5 wherein the surfaces are convex curved surfaces.

9. The apparatus of claim 8 wherein the sample has a thickness and an unstressed radius of curvature and wherein:

the convex curved surfaces each have a radius of curvature at the point thereon that is greater than the thickness and less than the unstressed radius of curvature of the sample.

10. The apparatus of claim 5 wherein the grippers are inclined relative to each other and to the common longitudinal line.

11. The apparatus of claim 5 wherein the processor is programmed to control the motor to move the members apart at a first rate until a substantial increase is detected in the longitudinal tensile force measured by the load sensor and then at a second and lower rate.

12. An apparatus for testing the properties of a curved linear material comprising:

a pair of members, including a support member and a carrier member, mounted for relative longitudinal movement toward and away from each other to stress a sample of the material along a longitudinal line:

a motor having an output drive operatively linked between the support member and the carrier member so as to impart relative longitudinal movement between the carrier member and the support member;

a pair of grippers, each mounted on a respective one of the members and each positioned and oriented to receive and tightly grip opposite ends of a length of a sample of material having an arcuate unstressed curvature, each of the grippers having mounted adjacent thereto on the respective member a surface positioned between the grippers and proximate the sample gripped therein, each surface having a point thereon tangent to the longitudinal line spaced transversely of the grippers, each of the points thereby being relatively longitudinally moveable in direct relation to relative movement between the members;

an encoder operatively linked to the members to generate a displacement signal having discrete values each directly related to a relative distance between the points.

13. The apparatus of claim 12 wherein the program controlled processor includes programmed logic devices responsive to the stored displacement signal values and load signal values, as the members are moved apart, so as to:

determine, in response to a substantial decrease in the measured force, a displacement signal value and a force measurement value corresponding to the breaking of the material and associated respectively with the total elongation and tensile strength of the material;

determine, from a substantial increase in the rate of change of the measured force signal to rate of change of the displacement signal, a measured distance between the points on the surfaces that defines an initial length of the sample when the sample has straightened and begun to elastically elongate: and determine, from a significant decrease in the rate of change of the measured force signal to rate of change of the displacement signal, a displacement signal value corresponding to a measured distance between the points on the convex surfaces that corresponds to the beginning of plastic deformation of the sample and defines an elastic elongation of the material, and a force measurement value associated with the yield strength of the material.

14. The apparatus of claim 13 wherein:

the processor is programmed to derive a constant corresponding to an elastic modulus for the sample from a derived linear relation of the tensile force of a values of longitudinal force and distance at a distance approximately midway between the initial length and the elastic elongation.

15. The apparatus of claim 12 wherein the surfaces are convex curved surfaces.

16. The apparatus of claim 15 wherein the sample has a thickness and an unstressed radius of curvature and wherein:

the convex curved surfaces each have a radius of curvature at the point thereon that is greater than the thickness and less than the unstressed radius of curvature of the sample.

17. The apparatus of claim 12 wherein the grippers are inclined relative to each other and to the longitudinal line.

18. The apparatus of claim 12 wherein the processor is programmed to control the motor to move the members apart at a first rate until a substantial increase is detected in the longitudinal tensile force measured by the load sensor and then at a second and lower rate.

* * * * *